United States Patent [19]

Cudahy et al.

[11] Patent Number: 4,895,161

[45] Date of Patent: * Jan. 23, 1990

[54] TRANSPORTABLE DATA MODULE AND DISPLAY UNIT FOR PATIENT MONITORING SYSTEM

[75] Inventors: Michael J. Cudahy, Delray Beach, Fla.; Carlos De La Huerga, Shorewood, Wis.; Harold N. Arneson, Waukesha, Wis.; R. Thomas Divers, Mequon, Wis.; Barry J. Altman, Mequon, Wis.

[73] Assignee: Marquette Electronics, Milwaukee, Wis.

[*] Notice: The portion of the term of this patent subsequent to Dec. 29, 2004 has been disclaimed.

[21] Appl. No.: 112,469

[22] Filed: Oct. 19, 1987

Related U.S. Application Data

[62] Division of Ser. No. 912,359, Sep. 26, 1986, Pat. No. 4,715,385.

[51] Int. Cl.⁴ .............................................. A61N 5/00
[52] U.S. Cl. .................................... 128/710; 128/696; 128/630
[58] Field of Search ............... 128/696, 702, 709, 710, 128/695

[56] References Cited

U.S. PATENT DOCUMENTS

| D. 262,401 | 12/1981 | Hawes et al. | 128/712 |
|---|---|---|---|
| 3,690,313 | 9/1972 | Weppner et al. | 128/696 |
| 3,865,101 | 2/1975 | Saper et al. | 128/696 |
| 3,915,154 | 10/1975 | Cosentino | 128/898 |
| 4,051,522 | 9/1977 | Healy et al. | 358/86 |
| 4,053,951 | 10/1977 | Hudspeth et al. | 364/415 |
| 4,216,462 | 8/1980 | McGrath et al. | 340/150 |
| 4,223,683 | 9/1980 | Lown et al. | 128/706 |
| 4,250,888 | 2/1981 | Grosskopf | 128/702 |
| 4,331,962 | 5/1982 | Neumann | 128/712 |
| 4,378,021 | 3/1983 | Strand | 128/710 |
| 4,417,306 | 11/1983 | Citron et al. | 364/415 |
| 4,530,066 | 7/1985 | Ohwaki et al. | 364/708 |
| 4,546,436 | 10/1985 | Schneider et al. | 364/415 |
| 4,654,818 | 3/1987 | Wetterau, Jr. | 364/900 |
| 4,688,579 | 8/1987 | Inahara | 128/695 |
| 4,715,385 | 12/1987 | Cudahy et al. | 128/710 |

OTHER PUBLICATIONS

Product Data Sheet—Physio Control VSM1 Vital Signs Monitor (1981).
Product Data Sheet—the Datascope 2000 Series Anesthesia Monitors (1983).
Product Data Sheet—the Hewlett Packard 78353B Patient Monitor (1983).
Product Data Sheet—the Spacelabs Model 514 Monitor (1981).

*Primary Examiner*—Francis Jaworski
*Assistant Examiner*—George Manuel
*Attorney, Agent, or Firm*—Andrus, Sceales, Starke & Sawall

[57] ABSTRACT

A monitoring system for providing continuous monitoring of a patient, including periods of transport, includes a data acquisition and processing module receiving physiological data from the patient. The module may be inserted in a bedside display unit to display the physiological condition data being monitored. The module may also be inserted in a portable display unit that can accompany the patient during transport. Connectors permit the module to simultaneously drive both the display units so that no data is lost when the module is removed from the bedside unit and placed in the portable unit and vice versa.

9 Claims, 2 Drawing Sheets

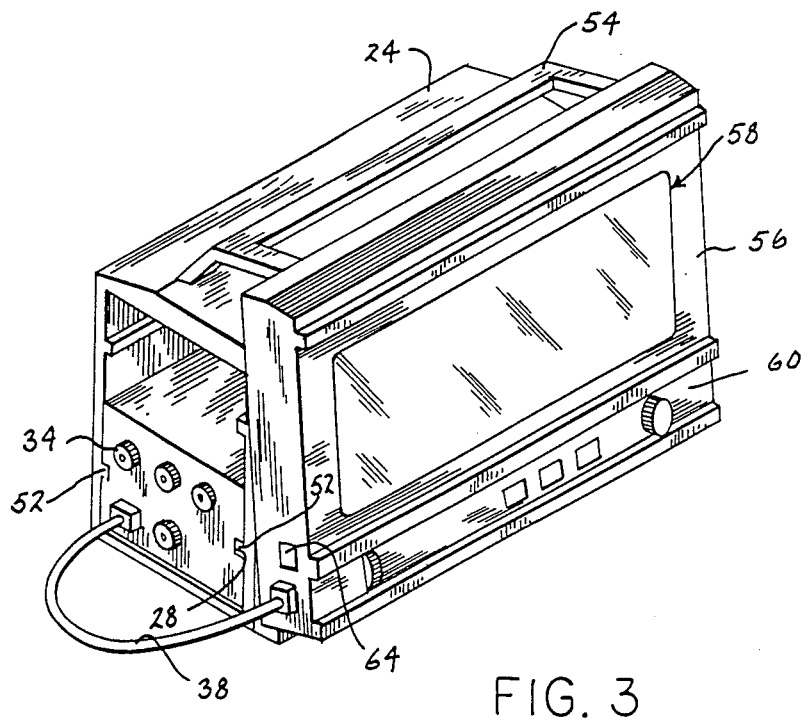
FIG. 3
FIG. 4
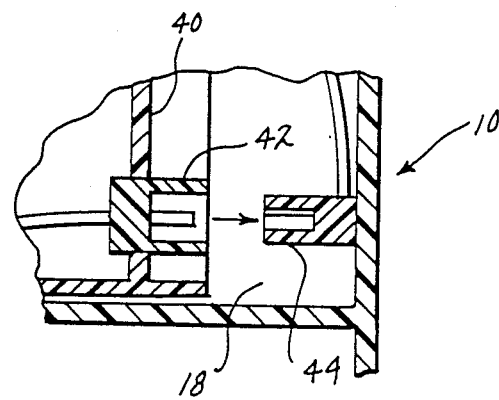

TRANSPORTABLE DATA MODULE AND DISPLAY UNIT FOR PATIENT MONITORING SYSTEM

The present application is a divisional application of U.S. patent application Ser. No. 06/912,359, filed Sept. 26, 1986 and now U.S. Pat. 4715385.

The present invention relates to a system for providing continuous physiological condition monitoring of a patent, including periods during which the patient is in transport from one location to another.

In a hospital or other health care setting, it is frequently necessary to observe critical physiological conditions of a patient, such as temperature, breath rate, pulse, blood pressure, ECG data, and cardiac output. Other conditions may be observed, depending on the injury or illness of the patient.

The physiological condition data is obtained by sensors applied to the patient. The sensors are connected to a monitor by cables. The monitor is mounted beside the patient's bed. The monitor is energized by power mains and displays the physiological condition data in graphic and/or alpha-numeric form so that it can be observed. The monitor is connected to a central system for recording the data.

It is usually necessary or desirable to continuously observe the patient's physiological condition in order to detect the onset of changes. However, due to the stationary nature of a bedside or surgical monitor, it is difficult to maintain continuous surveillance when the patient must be moved, as, for example, from the operating room to the recovery room, from the recovery room to the intensive care unit, or from the intensive care unit to his/her hospital room. It is possible to use another monitor at these times having a battery power supply. However, this requires disconnecting the stationary monitor and connecting the additional monitor at the beginning of transport and carrying out the reverse procedure at the end of transport. This is time consuming; provides the possibility for error; loses set up data, scalars, trend data, alarm limits and the like; and may interrupt continuous monitoring as the sensors are connected and disconnected. The additional monitor will usually not be compatible with the stationary monitor or central data processing system, causing problems in handling of the physiological condition data.

For the foregoing reasons, patients may not be monitored adequately, or at all, for a critical physiological condition at certain times, such as during transport.

It is, therefore, the object of the present invention to provide a physiological condition monitoring system that can provide continuous, uninterrupted, monitoring of a patient, including periods when the patient is in transport.

The monitoring system of the present invention is simple and easy to use and avoids the multiple connection and disconnection of sensors heretofore required. It maintains all setup data, alarm limits, scalars, and the like during monitoring of the patients.

Briefly, the present invention contemplates a monitoring system including a substantially non-transportable, or stationary, first display unit positioned, for example, in the recovery room for providing a display of physiological condition data being monitored. A portable, second display unit is capable of accompanying the patient during transport also for providing a display of physiological data being monitored. A data acquisition and processing module receives physiological condition data from the patient. The module is capable of being used in conjunction with either the first or second display units. Connection means are provided to couple the module to either or both of the first and second display units to display the data of the physiological conditions being monitored.

In use, the data acquisition and processing module is typically received in the non-transportable unit when the patient is, for example, in the recovery room. When the patient is to be moved, the module is additionally connected to the portable, second display unit so that physiological condition data is displayed on both units. The module is then removed from the non-transportable display unit and placed in the portable display unit to accompany the patient during transport. At the completion of the transport, the operative sequence is reversed.

The invention will be further understood, and appreciated, from the following detailed description, taken in conjunction with the drawing in which:

FIG. 3 shows the monitoring system of the present invention when the data acquisition and processing module is mounted in the portable display unit; and FIG. 4 is a fragmentary view of a portion of the module and non-transportable display unit showing a connector on the module and a corresponding connector on the non-transportable display unit.

Figure 1:
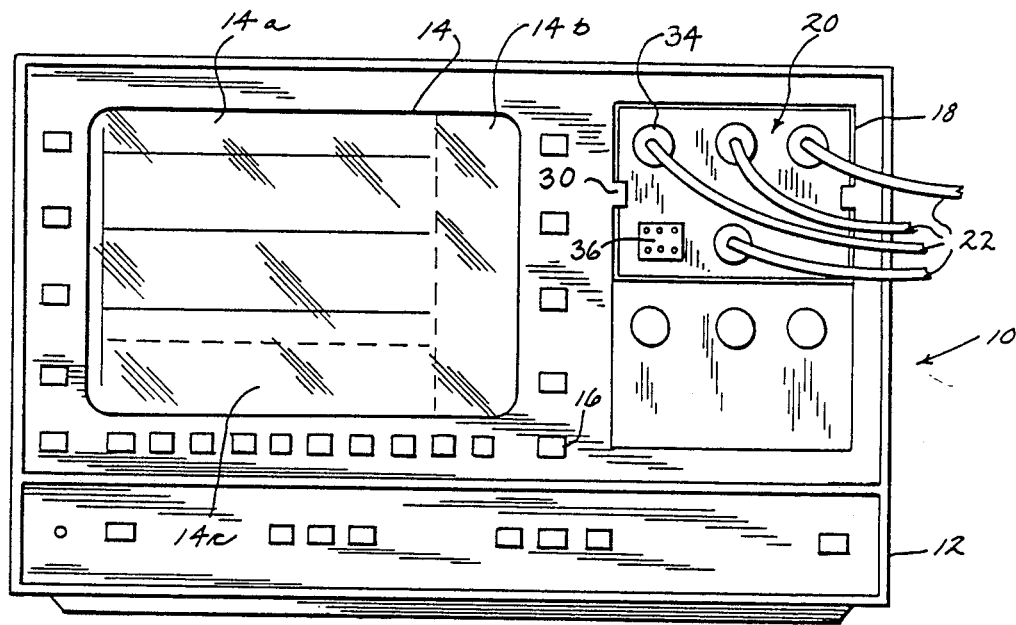
FIG. 1 shows the patient monitoring system of the present invention when the data acquisition and processing module is received in the generally non-transportable beside/surgical monitor.

FIG. 1 shows a generally non-transportable monitor or display unit 10. Display unit 10 is typically mounted on the wall at the patient's bed in an operating room, recovery room, intensive care unit, hospital room or other care facility. The unit is energized by a power cord, not shown, from conventional power mains. Display unit 10 includes housing 12 having screen 14 on which physiological data can be displayed in graphic or alpha-numeric form in a predetermined manner. Typically, the screen will include a portion 14a graphically displaying a plurality of physiological data as wave forms, a portion 14b displaying certain values such as heart rate, blood pressure, and temperature in numerical form, and a menu portion 14c in which commands, data requests, and the like are displayed. Display unit 10 contains a microprocessor or other circuitry for operating the monitor and for driving screen 14. A plurality of control elements, such as button 16, control the circuitry in display unit 10 to control the operation of the monitor, the display of physiological condition data, the setting of alarm limits for such conditions, and the like. An audible alarm may be provided in display unit 10 that sounds when the limits are exceeded. Display unit 10 contains a recess 18 for receiving data acquisition and processing module 20.

Digital acquisition and processing module 20 accepts inputs from sensor cables 22 connected to the patient, processes the input data to derive waveforms and values therefrom, and provides an physiological condition data signal output for driving the display of either non-transportable display unit 10 or a separate portable display unit 24, hereinafter described. Module 20 also stores data, such as alarm limits, obtained from the control element of the display unit.

Module 20 has housing 26 for containing the physiological condition data acquisition and processing circuitry of conventional construction necessary to obtain the physiological condition data signal output, establish alarm limits, and the like. Housing 26 also includes a battery for powering the circuitry. The battery is typically of the rechargeable lead-acid type. Housing 26 has grooves 28 that assist in positioning the module in the display unit. Grooves 28 mate with ridges 30 of recess 18 in non-transportable display unit 10.

Front panel 32 of module 20 contains input connectors 34 for receiving sensor cables 22. Front panel 32 may also contain a battery charge indicator for indicating when the battery is being recharged. Front panel 32 has jack 36 for a cord 38 for connecting module 20 to portable display unit 24, in the manner shown in FIG. 3. Front panel 32 may also contain output jacks that provide direct outputs of desired data, such as ECG or blood pressure, to recording writers, or other equipment.

Rear panel 40 of module 20 shown in FIG. 4 contains a pin type connector 42 that mates with a corresponding connector 44 in the back of recess 18 of display unit 10. Connectors 42 and 44 supply power and data to, and receive data from, module 20, when the module is inserted in recess 18 of display unit 10. Connectors 42, 44 may also supply power to a battery charging circuit in module 20.

Figure 2:
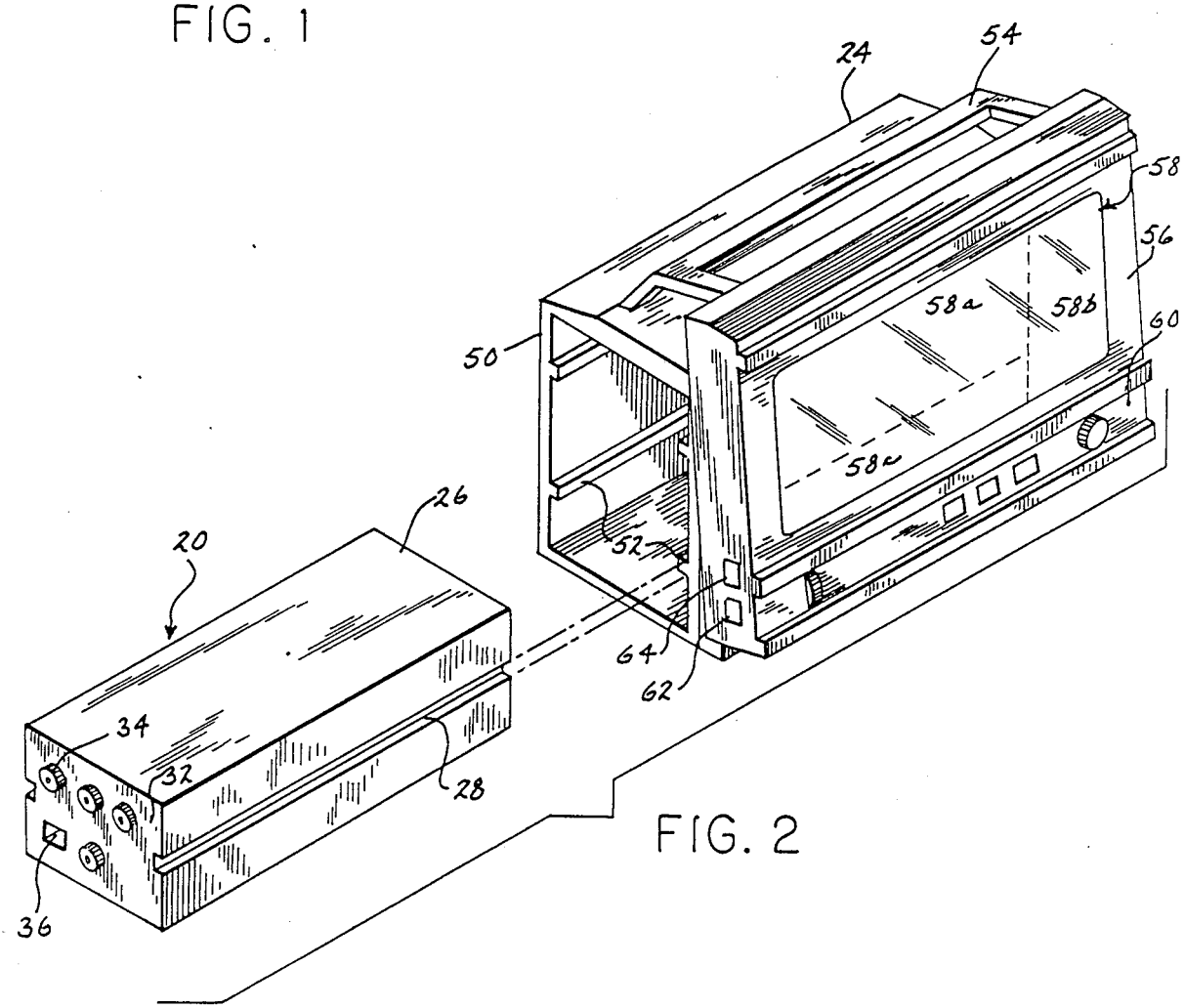
FIG. 2 shows the module and the manner of inserting same in the portable display unit.

Portable display unit 24 includes base member 50. Base member 50 has a rectangular tubular configuration. Base member 50 is closed by a vertical wall at one end, i.e. the right-hand end, as shown in FIGS. 2 and 3, to form a compartment for receiving the data acquisition and processing module 20, in the manner shown in FIG. 3. Guide rails 52 on the inside of base member 50 mate with grooves 28 on module 20 to assist in positioning the module in the compartment of base member 50. Portable display unit 24 is shown in FIGS. 2 and 3 with a compartment large enough to receive another module, such as one containing a writer for recording physiological condition data, if desired. Or portable display unit 24 may be formed so that the compartment is sized only to receive module 20.

Handle 54 is fastened to base member 50 so that portable display unit 24 and the module or modules in the compartment of base member 50 may be lifted or moved.

Screen element 56 is mounted on one side of base member 50 and is of the "flat panel" type or configuration. Screen element 56 includes screen 58 which may be of the liquid crystal display type or may be of the electroluminescent, plasma or gas discharge, or other type. Screen 58 may be operated and controlled by a microprocessor or other circuitry in portable display unit 24. The format of screen 58 resembles that of screen 14 of monitor 10 and displays the same physiological condition data. Screen 58 thus includes a portion 58a graphically displaying the physiological condition data as wave forms, a portion displaying values in numerical form, and a menu portion 58c. Screen member 56 also contains control panel 60 for screen 58 and data acquisition and processing module 20. Typical controls include a contrast control for screen 58, an alarm reset control to silence an audio alarm in the display unit, a freeze control to halt waveform movement, a blood pressure zero control, and a control for accessing and displaying menus used to operate the monitor, for example to set limit values for the physiological conditions being monitored. The control action provided by portable display unit 24 thus generally corresponds to that of non-transportable display unit 10.

Portable display unit 24 also includes connection jack 62 for cable 38. One or more auxiliary connection jacks 64 may be provided for peripheral equipment. Such peripheral equipment may include a printer or a remote control cable that permits accessing and operating portable display unit 24 from a remote location.

Typical usage of the monitoring system of the present invention is described below in connection with a patient on a wheeled stretcher or gurney in a surgical recovery room. Module 20 is located in recess 18 of display unit 10. Module 20 is energized through connectors 42 and 44. The sensors of cables 22 are applied to the patient. Cables 22 are inserted in the appropriate connectors 34 on the front panel 32 of data acquisition and processing module 20. The controls 16 of monitor 10 are operated to provide set-up data, such as alarm limits, calibration data, etc. for storage in module 20.

Data acquisition and processing module 20 receives data from cables 22 and provides signals through connectors 42, 44 for driving display 14 of display unit 10 so that the physiological condition data may be observed by attending medical and nursing personnel.

When it is desired to transport the patient, one end of cord 38 is connected in jack 36 of module 20. The other end is connected to jack 62 of portable display unit 24. The controls of control panel 60 are manipulated to turn on display unit 24 so that the physiological condition data appears on screen 58. Module 20 thus drives screen 58 of portable display unit 24 in addition to screen 14 of display unit 10.

Module 20 is then removed from recess 18 of display unit 10 and placed in the compartment of base member 50 of portable display unit 24, in the manner shown in FIG. 2. Module 20 is powered by its internal storage battery. Display unit 10 is turned off.

Portable display unit 24 containing module 20 may then be placed on the patient's stretcher for transport with the patient to his/her hospital room. Monitoring of the patient's physiological condition is obtained by means of screen 58 of portable display unit 24 during transport. In the hospital room, the patient is removed from the stretcher and placed on his/her bed. Portable display unit 24 is similarly moved so that monitoring is continued.

If long term monitoring is desired, a non-transportable display unit 10, similar to that described above, proximate to the patient's bed may be employed. Module 20 is removed from the base member 50 of display unit 24 and placed in recess 18 of the new display unit 10. Cord 38 remains connected between module 20 and display unit 24. Display unit 10 is then turned on so that module 20 provides physiological condition data on screen 14 as well as on screen 58. Thereafter, screen 58 may be turned off and cord 38 removed from jacks 36 and 62. Further monitoring is carried out on display unit 10.

While module 20 is described above as placed in the compartment in portable display unit 24, it will be appreciated that this is not necessary. For example, module 20 may be placed near the patient and display unit 24, without the module, placed on a shelf for greater visibility, if desired. Module 20 and display unit 24 remain connected by cord 38. Also, while the patient monitoring system of the present invention has been described in a hospital setting, it will be appreciated that it may be used in other settings, such as ambulance or aircraft transport.

From the foregoing description, it will be apparent that the monitoring system of the present invention is capable of providing continuous monitoring of a patient, including periods when the patient is being transported. This is accomplished by the ability of the monitoring system of the present invention to drive both display units 10 and 24 simultaneously, when needed. It is also accomplished by the ability of module 20 to be removed from non-transportable display unit 10 and placed in, or in proximity to, separate transportable display unit 24, and vice versa.

Various modes of carrying out the invention are contemplated as being within the scope of the following claims particularly pointing out and distinctly claiming the subject matter which is regarded as the invention.

We claim:

1. A portable monitor unit for receiving and displaying physiological condition data of a patient, the patient having physiological condition data sensors applied thereto, said portable monitor unit being usable in conjunction with a unit not intended for transport for making possible a continuous display of physiological condition data, said unit not intended for transport displaying the physiological condition data in a predetermined manner, said unit not intended for transport having a recess of predetermined dimensions, said portable monitor unit comprising:

a module for receiving data from the sensors and having circuitry for processing the received data, said module having an exterior configuration with dimensions corresponding with dimensions of said recess so that said module may be inserted in said recess in the unit not intended for transport, said module having first data output connection means capable of coupling said module to the unit not intended for transport for providing a first plurality of physiological condition data to said unit not intended for transport, said module having second data output connection means providing a second plurality of physiological condition data, the data of said second plurality including at least a portion of the data of the first plurality;

a power supply operatively associated with said module for energizing said circuitry;

a portable member having means for removably retaining said module with said portable member, said portable member having a screen for displaying physiological condition data in a manner compatible with that of the unit not intended for transport; and means for connecting said second data output connection means of said module to said portable member for providing, from said module to said member, said second plurality of physiological condition data so that said module may operate said screen to display physiological condition data.

2. The portable display unit according to claim 1 wherein said means for connecting said second data output connection means to said portable member comprises a connection cord.

3. The portable monitor unit according to claim 1 wherein said portable member screen comprises a flat panel display.

4. The portable monitor unit according to claim 3 wherein said screen includes a graphic display portion, an alpha-numeric display portion, and a menu portion.

5. The portable monitor unit according to claim 1 wherein said portable member has a carrying handle.

6. The portable display unit according to claim 1 wherein said screen is integral with said portable member.

7. The portable display unit according to claim 1 wherein said portable member has a compartment corresponding to said recess in said unit not intended for transport for removably receiving said module within said compartment.

8. The portable monitor unit according to claim 7 wherein said compartment of said portable member is sufficiently large to receive said module and a second object having the shape of said module.

9. A portable monitor unit for receiving and displaying physiological condition data of a patient, the patient having physiological condition data sensors applied thereto, said portable monitor unit being usable in conjunction with a unit not intended for transport for making possible a continuous display of physiological condition data, said unit not intended for transport displaying the physiological condition data in a predetermined manner, said unit not intended for transport having a recess of predetermined dimensions, said portable monitor unit comprising:

a module for receiving data from the sensors and having circuitry for processing the received data, said module having an exterior configuration with dimensions corresponding with dimensions of said recess so that said module may be inserted in said recess in the unit not intended for transport, said module having first data output connection means capable of coupling said module to the unit not intended for transport for providing a first plurality of physiological condition data to said unit not intended for transport, said module having second data output connection means providing a second plurality of physiological condition data, the data of said second plurality including at least a portion of the data of the first plurality;

a power supply operatively associated with said module for energizing said circuitry;

a portable base member having a compartment corresponding to said recess in the unit not intended for transport for removably receiving said module within said compartment, said base member having an integral screen for displaying physiological condition data in a manner compatible with that of the unit not intended for transport; and means for connecting said second data output connection means of said module to said base member for providing, from said module to said base member, said second plurality of physiological condition data so that said module may operate said screen to display physiological condition data.

* * * * *